United States Patent [19]

Urdea

[11] Patent Number: 5,631,148

[45] Date of Patent: May 20, 1997

[54] RIBOZYMES WITH PRODUCT EJECTION BY STRAND DISPLACEMENT

[75] Inventor: Michael S. Urdea, Alamo, Calif.

[73] Assignee: Chiron Corporation, Emeryville, Calif.

[21] Appl. No.: 231,227

[22] Filed: Apr. 22, 1994

[51] Int. Cl.$^6$ .............................. C12P 19/34; C12Q 1/68; C07H 21/00; C07H 21/04
[52] U.S. Cl. .................. 435/91.31; 435/6; 435/172.1; 536/23.1; 536/23.2; 536/24.5
[58] Field of Search .......................... 435/6, 91.2, 91.3, 435/91.31, 91.4, 172.1, 199, 320.1; 514/44; 536/23.1, 23.2, 24.5, 25.3

[56] References Cited

U.S. PATENT DOCUMENTS

| | | | |
|---|---|---|---|
| 4,818,680 | 4/1989 | Collins et al. | 435/6 |
| 4,987,071 | 1/1991 | Cech et al. | 435/91.31 |
| 5,037,746 | 8/1991 | Cech et al. | 435/91.31 |
| 5,093,246 | 3/1992 | Cech et al. | 435/6 |
| 5,116,742 | 5/1992 | Cech et al. | 435/91.31 |
| 5,144,019 | 9/1992 | Rossi et al. | 536/23.1 |
| 5,168,053 | 12/1992 | Altman et al. | 514/44 |
| 5,180,818 | 1/1993 | Cech et al. | 536/23.1 |
| 5,225,337 | 7/1993 | Robertson et al. | 435/91.31 |
| 5,225,347 | 7/1993 | Goldberg et al. | 435/320.1 |
| 5,254,678 | 10/1993 | Haseloff et al. | 536/23.2 |
| 5,436,330 | 7/1995 | Taira et al. | 536/23.2 |

FOREIGN PATENT DOCUMENTS

| | | |
|---|---|---|
| 92/13070 | 6/1992 | WIPO . |
| 94/01550 | 1/1994 | WIPO . |

OTHER PUBLICATIONS

United States Biochemical Corp Catalog, p. 177.
Taira et al., "Construction of a novel artificial–ribozyme–releasing plasmid", *Protien Eng.* 3(8):733–737 (1990).
David P. Bartel and Jack W. Szostak: Isolation of New Ribozymes From a Large Pool of Random Sequences; *Science*, vol. 261; pp. 1411–1418; Sep. 10, 1993.
Malcolm J. Bennett and Julie V. Cullimore: Selective Cleavage of Closely–Related mRNAs by Synthetic Ribozymes; *Nucleic Acids Research*, vol. 20, No. 4, 831–837; 1992.
J.M. Buzayan, W. L. Gerlach and G. Bruening: Non–Enzymatic Cleavage and Ligation of RNAs Complementary to a Plant Virus Satellite RNA; *Nature*, vol. 323; pp. 349–353; Sep. 25, 1986.
J.M. Buzayan, A. Hampel & G. Bruening: Nucleotide Sequence and Newly Formed Phosphodiester Bond of Spontaneously Ligated Satellite Tobacco Ringspot Virus RNA; *Nucleic Acids Research*, vol. 14, No. 24, pp. 9729–9743, 1986.
T.A. Cha, J. Kolberg, B. Irvine, M. Stempien, E. Beall, M. Yano, Q. Choo, M. Houghton, G. Kuo, J.H. Han, and M.S. Urdea: Use of a Signature Nucleotide Sequence of Hepatitis C Virus for Detection of Viral RNA in Human Serum and Plasma; *Journal of Clinical Microbiology*, vol. 29, No. 11, pp. 2528–2534, Nov. 1991.

T.–A.Cha, E. Beall, B. Irvine, J. Kolberg, D. Chien, G. Kuo, and M.S. Urdea: At Least Five Related, But Distinct, Hepatitis C Viral Genotypes Exist; *Proc. Natl. Acad. Sci. USA*, vol. 89, pp. 7144–7148, Aug. 1992.
B.M. Chowrira and J.M. Burke: Extensive Phosphorothioate Substitution Yields Highly Active and Nuclease–Resistant Hairpin Ribozymes; *Nucleic Acids Research*, vol. 20, No. 11, 2835–2840, 1992.
M. Cotten, G. Schaffner, and M.L. Birnstiel: Ribozxyme, Antisense RNA, and Antisense DNA Inhibition of U7 Small Nuclear Ribonucleoprotein–Mediated Histone Pre–mRNA Processing In Vitro; *Molecular and Cellular Biology*, vol. 9, No. 10, pp. 4479–4487, Oct. 1989.
M.J. Fedor and O.C. Uhlenbeck: Kinetics of Intermolecular Cleavage by Hammerhead Ribozymes; *Biochemistry*, 31, 12042–12054, 1992.
John Goodchild and Vipin Kohli: Ribozymes That Cleave an RNA Sequence from Human Immunodeficiency Virus: The Effect of Flanking Sequence on Rate; *Archives of Biochemistry and Biophysics*, vol. 284, No. 2, pp. 386–391, Feb. 1, 1991.
John Goodchild: Enhancement of Ribozyme Catalytic Activity by a Contiguous Oligodeoxynucleotide (Facilitator) and by 2'–O–methylation; *Nucleic Acids Research*; vol. 20, No. 17, 4607–4612; 1992.
J.A. Grasby, P. Jonathan G. Butler and Michael Gait: The Synthesis of Oligoribonucleotides Containing $O^6$–methylguanosine: The Role of Conserved Guanosine Residues in Hammerhead Ribozyme Cleavage; *Nucleic Acids Research*, vol. 21, No. 19, pp. 4444–4450; Aug. 1993.
Sergei M. Gryaznov and David H. Lloyd: Modulation of Oligonucleotide Duplex and Triplex Stability Via Hydrophobic Interactions; *Nucleic Acids Research*, vol. 21, No. 25, 5909–5915, 1993.
Arnold Hampel and Richard Tritz: RNA Catalytic Properties of the Minimum (–)s TRSV Sequence; *Biochemistry*, vol. 28, No. 12, 4929–4933, 1989.
Jim Haseloff and Wayne L. Gerlach: Simple RNA Enzymes With New and Highly Specific Endoribonuclease Activities; *Nature*, vol. 334, pp. 585–591; Aug. 18, 1988.
Jim Haseloff and Wayne L. Gerlach: Sequences Required for Self–Catalyzed Cleavage of the Satellite RNA of Tobacco Ringspot Virus; *Gene*, 82, 43–52, 1989.

(List continued on next page.)

*Primary Examiner*—John L. LeGuyader
*Assistant Examiner*—Thomas G. Larson
*Attorney, Agent, or Firm*—Laura A. Handley; Kenneth M. Goldman; Robert P. Blackburn

[57] ABSTRACT

Ribozymes designed to provide improved rates of catalytic turnover are described. The compounds of this invention comprise a catalytic region, at least one substrate binding region, and at least one displaceable antisense arm, whereby the rate of release of the endonuclease cleavage fragments is enhanced. A method to make such ribozymes is also described.

28 Claims, 3 Drawing Sheets

OTHER PUBLICATIONS

Olaff Heidenreich and Fritz Eckstein: Hammerhead Ribozyme-mediated Cleavage of the Long Terminal Repeat RNA of Human Immunodeficiency Virus type 1; *The Journal of Biological Chemistry*, vol. 267, No. 3, pp. 1904–1909, Jan. 25, 1992.

Olaf Heidenreich, Wolfgang Pieken and Fritz Eckstein: Chemically Modified RNA: Approaches and Applications; *The FASEB Journal*, vol. 7, pp. 90–96, Jan. 1993.

Philip Hendry, Maxine J. McCall, Fernando S. Santiago and Philip A. Jennings: Ribozyme with DNA in the Hybridizing Arms Displays Enhanced Cleavage Ability; *Nucleic Acids Research*, vol. 20, No. 21, pp. 5737–5741, 1992.

K.J. Hertel, A. Pardi, O.C. Uhlenbeck, M. Koizumi, E. Ohtsuka, S. Uesugi R. Cedergren, F. Eckstein, W.L. Gerlach, R. Hodgson and R.H. Symons: Numbering System for the Hammerhead; *Nucleic Acids Research*, vol. 20, No. 12, p. 3252, 1992.

Alex C. Jeffries and Robert W. Symons: A Catalytic 13-mer Ribozyme; *Nucleic Acids Research*, vol. 17, No. 4, pp. 1371–1377, 1989.

Makoto Koizumi, Shigenori Iwai and Eiko Ohtsuka: Cleavage of Specific Sites of RNA by Designed Ribozymes; *FEBS Letters*, vol. 239, No. 2, pp. 285–288; Nov. 1988.

Makoto Koizumi and Eiko Ohtsuka: Effects of Phosphorothioate and 2-Amino Groups in Hammerhead Ribozymes on Cleavage Rates and $Mg^{2+}$ Binding; *Biochemistry*, vol. 30, No. 21, 51450–5150, 1991.

Makoto Koizumi, Yoji Hayase, Shigenori Iwai Hiroyuki Kamiya, Hideo Inoue and Eiko Ohtsuka: Design of RNA Enzymes Distinguishing a Single Base Mutation in RNA; *Nucleic Acids Research*, vol. 17, No. 17, pp. 7059–7071, 1989.

J.W. Lamb and R.T. Hay: Ribozymes That Cleave Potato Leafroll Virus RNA Within the Coat Protein and Polymerase Genes; *Journal of General Virology*, 71, pp. 2257–2264, 1990.

David M. Long and Olke C. Uhlenbeck: Self-Cleaving Catalytic RNA; *The FASEB Journal*, vol. 7, pp. 25–30, Jan. 1993.

Joshua O. Ojwang, Arnold Hampel, David J. Looney, Flossie Wong-Staal, and Jay Rappaport: Inhibition of Human Immunodeficiency Virus Type 1, Expressions By A Hairpin Ribozyme; *Proc. Natl. Acad. Sci. USA*, vol. 89, pp. 10801–10806, Nov. 1992.

David B. Olsen, Fritz, Benseler, Helle Aurup, Wolfgang A. Pieken and Fritz Eckstein: Study of Hammerhead Ribozyme Containing 2'-Modified Adenosine Residues; *Biochemistry*, vol. 30, pp. 9735–9741, 1991.

Jean-Pierre Perreault, Taifeng Wu, Benoit Cousineau, Kelvin K. Ogilvie and Robert Cetergren: Mixed Deoxyribo-and Ribo-Oligonucleotides with Catalytic Activity; *Nature*, vol. 344, pp. 565–567, Apr. 5, 1990.

Jean-Pierre Perreault, Damian Labuda, Nassim Usman, Jig-Hua Yang and Robert Cedergren: Relationship Between 2'-Hydroxyls and Magnesium Binding in the Hammerhead RNA Domain: A Model for Ribozyme Catalysis: *Biochemistry* vol. 30, No. 16, pp. 4020–4025, 1991.

Anne T. Perrotta and Michael D. Been: Cleavage of Oligoribonucleotides by a Ribozyme Derived from the Hepatitis Virus RNA Sequence, *Biochemistry*, vol. 31, No. 1, pp. 16–21, 1992.

Giovanni Paolella, Biran S. Sproat and Angus I. Lamond: Nuclease Resistant Ribozymes with High Catalytic Activity: *The EMOB Journal*, vol. 11, No. 5, pp. 1913–1919, 1992.

Wolfgang A. Pieken, David B. Olsen, Fritz Benseler, Heele Aurup, Fritz Eckstein: Kinetic Characterization of Ribonuclease-Resistant 2'-Modified Hammerhead Ribozymes; *Science*, vol. 253, pp. 314–317, Jul. 19, 1991.

Gerry A. Prody, John T. Bakos, Jamal M. Buzayan, Irving R. Schneider, George Bruening: Autolytic Processing of Dimeric Plant Virus Satellite RNA; *Science*, vol. 231, pp. 1577–1580; Mar. 28, 1986.

Duane E. Ruffner and Olke C. Uhlenbeck: Thiophosphate Interference Experiments Locate Phosphates Important for the Hammerhead RNA Self-Cleavage Reaction; *Nucleic Acids Research*, vol. 18, No. 20, pp. 6025–6029; 1990.

Susumu Shibahara, Sachiko Mukai, Hirokaza Morisawa, Kideki Nakashima, Susumu Kobayashi and Naoki Yamamoto: Inhibition of Human Immunodeficiency Virus (HIV-1) Replication by Synthetic Oligo-RNA Derivatives; *Nucleic Acids Research*, vol. 17, No. 1, pp. 239–252, 1989.

George Slim and Michael J. Gait: Configurationally Defined Phosphorothioate-Containing Oligoribonucleotides in this Study of the Mechanism of Cleavage of Hammerhead Ribozymes; *Nucleic Acids Research*, vol. 19, No. 6, pp. 1183–1188; 1991.

Robert H. Symons: Small Catalytic RNAs; *Annu. Rev. Biochem*, 61:641–71, 1992.

Robert H. Symons: Self-Cleavage of RNA in the Replication of Small Pathogens of Plants and Animals; *Trends in Biochemical Sciences*, vol. 14, No. 11, pp. 445–450, Nov. 1989.

Nerida R. Taylor, Bruce E. Kaplan, Piotr Swiderski, Haitang Li, and John J. Rossi: Chimeric DNA-RNA Hammerhead Ribozymes have Enhanced in vitro Catalytic Efficiency and Increased Stability in vivo; *Nucleic Acids Research*, vol. 20, No. 17, 4559–4565; 1992.

Zenta Tsuchihashi, Mala Kohola, Daniel Herschlag: Protein Enhancment of Hammerhead Ribozyme Catalysis: *Science*, vol. 262, pp. 99–102, Oct. 1, 1993.

Olke C. Uhlenbeck: A Small Catalytic Oligoribonucleotide; *Nature*, vol. 328, pp. 596–600, Aug. 1987.

David M. William, Wolfgang A. Pieken and Fritz Eckstein: Function of Specific 2'-hydroxyl Groups of Guanosines in a Hammerhead Ribozyme Probed by 2' Modifications; *Proc. Natl. Acad. Sci. USA*, vol. 89, pp. 918–922, Feb. 1992.

G. Terrance Walker, Melinda S. Fraiser, James L. Schram, Michael C. Little, James G. Nadeau, and Douglas P. Malinowski: Strand Displacement Amplification—An Isothermal in vitro DNA Amplification Technique; *Nucleic Acids Research*, vol 20, No. 7, 1691–1696, 1992.

George Y. Wu and Catherine H. Wu: Specific Inhibition of Hepatitis B. Viral Gene Expression in vitro by Targeted Antisense Oligonucleotides; *The Journal of Biological Chemistry*, vol. 267, No. 18, pp. 12436–12439, Jun. 1992.

Jing–hua Yang, Nassim Usman, Pascal Chartrand, and Robert Cedergren; Minimum ribonucleotide Requirement for Catalysis by the RNA Hammerhead Domain; *Biochemistry*, vol. 31, No. 21, pp. 5005–5009, 1992.

Mang Yu, Joshua Ojwang, Osamu Yamada, Arnold Hampel, Jay Rapapport, David Looney, and Flossie Wong-Staal: A Hairpin Ribozyme Inhibits Expression of Diverse Strains of Human Immunodeficiency Virus Type 1; *Proc. Natl. Acad. Sci. USA*, vol. 90, pp. 6340–6344, Jul. 1993.

RIBOZYMES WITH PRODUCT EJECTION BY STRAND DISPLACEMENT

BACKGROUND OF THE INVENTION

1. Field of the Invention

This invention relates to compounds known as ribozymes.

Ribozymes are polynucleotides which "have the intrinsic ability to break and form covalent bonds." Symons, *Ann. Rev. Biochem.* 61:641 (1992). Of primary interest here are ribozymes which break bonds—that is, which cleave a long polynucleotide strand into two cleavage fragments. The first ribozymes were thought to act only upon RNA, but ribozymes that cleave single-stranded DNA have recently been reported. Cech et al., U.S. Pat. No. 5,180,818, the disclosure of which is incorporated by reference.

Ribozymes are valuable in vivo therapeutic agents that inactivate target RNA or DNA within the cell. In particular, ribozymes are exciting therapeutic candidates for AIDS. In vivo applications of ribozymes have been described in U.S. Pat. No. 5,254,678, U.S. Pat. No. 5,225,337, U.S. Pat. No. 5,168,053, and U.S. Pat. No. 5,144,019, the disclosures of which are incorporated by reference herein.

Ribozymes also can be efficient in vitro experimental reagents akin to restriction endonucleases, giving a researcher the ability to cleave a polynucleotide at a particular site. In vitro applications of ribozymes have been described in, e.g., U.S. Pat. No. 5,225,337, U.S. Pat. No. 5,180,818, U.S. Pat. No. 5,093,246, U.S. Pat. No. 5,037,746, and U.S. Pat. No. 4,987,071, the disclosures of which are incorporated by reference herein.

Ribozymes have the potential to serve as "catalysts" of chemical reactions, either in vitro or in vivo. In general, a catalyst will assist and/or drive the chemical reaction, without itself being altered in the process. After a catalytic event, the catalyst may be regenerated and is able to assist in another round of chemical reaction. Catalytic reactions may be more specifically described by two parameters—the specificity of a catalyst to selectively interact only with a particular substrate molecule, and the relative ability of a catalyst to alter the kinetics or rate at which a chemical reaction proceeds. Thus a ribozyme, like other catalysts such as protein-based enzymes, may be characterized in terms of both its kinetics and its specificity. Particularly useful ribozymes, like protein-based enzymes, will combine the qualities of being able to act rapidly and with good specificity.

2. Description of the Problem

The first ribozyme was described by Thomas Cech and colleagues in 1982, and was isolated from *Tetrahymena thermophila*. Kruger et al., *Cell* 31:147 (1982); U.S. Pat. No. 5,180,818; U.S. Pat. No. 5,116,742; U.S. Pat. No. 5,093,246; U.S. Pat. No. 5,037,746; U.S. Pat. No. 4,987,071. The Tetrahymena ribozyme catalyzed the excision of an intervening sequence (termed an IVS or intron) from within its own RNA, and subsequently ligated the two remaining exons. Other ribozymes of this sort, referred to as "Group I introns," were subsequently identified. Symons, *Ann. Rev. Biochem.*, p. 642. A similar class of self-splicing ribozymes have been identified and denominated "Group II introns." Id. Because the cleavage reactions of Group I and Group II ribozymes are intramolecular and result in alteration of the ribozyme itself, they cannot be described as catalytic. These ribozymes may be termed "native" ribozymes.

Another broad class of native ribozymes was discovered amongst various pathogenic plant RNAs. Long and Uhlenbeck, *FASEB J.* 7:25–30 (1993). Many of these native ribozymes have been described as "hammerhead" ribozymes, in reference to the secondary structure which the ribozymes assume. Symons, *Ann. Rev. Biochem.*, p. 645. Specifically, the hammerhead structure comprises a highly conserved nucleotide sequence in the region of catalytic activity. The catalytic region is substantially single-stranded RNA and is flanked by three regions of helical base-pairing. The endonuclease reaction catalyzed by the hammerhead ribozymes differs from that of the Group I, Group II, and RNAase P ribozymes in that it is a transesterification reaction producing a 5' hydroxyl and a 2',3'-cyclic phosphate. The native hammerhead ribozymes undergo intramolecular cleavage, with only a single turnover for each. Symons, *Ann. Rev. Biochem.*, p. 642.

Native ribozymes having other secondary structures have also been characterized. Hampel et al., *Biochemistry* 28:4929 (1989), describe a ribozyme which displays a secondary structure referred to as "hairpin." The hairpin structure, like the hammerhead structure, catalyzes cleavage via a transesterification reaction, and with similar stereochemical properties. Symons, *Ann. Rev. Biochem.*, p. 660. Like the hammerhead structure, the hairpin structure contains regions of highly conserved sequences, with the catalytic site in close proximity to a base-paired region. Id. at 661. Other researchers have identified a ribozyme in the Hepatitis Delta Virus (HDV), and have described the structure as an "axehead." Id. at 662–64. It too contains a highly conserved region, and it too contains several base-paired regions in close proximity to a single-stranded catalytic region. Id.

Following the discovery of native, non-catalytic ribozymes, researchers discovered native ribozymes capable of intermolecular cleavage reactions. In 1983, Guerrier-Takada et al. reported that the RNA component of RNAase P could cleave its tRNA substrate, even in the complete absence of protein. *Cell* 35:849 (1983). Soon thereafter, Cech et al. reported that a fragment of Tetrahymena catalyzed a number of transesterification reactions in a truly catalytic manner. Symons, *Ann. Rev. Biochem.*, p. 642.

Subsequently, Uhlenbeck and colleagues exploited the highly conserved catalytic region and the helical flanking regions of the hammerhead structure to design the first synthetic catalytic ribozyme. Symons, *Ann. Rev. Biochem.*, p. 647. Other examples of synthetic catalytic ribozymes based on the hammerhead structure followed. E.g., U.S. Pat. No. 5,254,678; Jeffries and Symons, *Nucl. Acids Res.*, 17:1371 (1989); and Koizumi et al., *FEBS Letters* 239:285 (1988). The hairpin structure has been exploited in the formation of a synthetic ribozyme which cleaves HIV-1 RNA. Ojwang et al., *Proc. Nat. Acad. Sci.* 89:10802 (1992); U.S. Pat. No. 5,144,019. The HDV ribozyme sequence and structure also has been characterized. Perrotta and Been, *Biochemistry* 31:16–21 (1992); U.S. Pat. No. 5,225,337.

In order to be of practical value, a ribozyme must act intermolecularly on a separate substrate molecule, and remain intact so as to act on subsequent substrate molecules. Ribozymes which perform such intermolecular reactions are termed catalysts, akin to the enzymatic proteins which catalyze myriad chemical reactions within the cell.

Ribozymes, like protein-based enzymes, may be characterized by the kinetic parameters of the reactions that they catalyze. The rate of catalysis may be described by one parameter designated $k_{cat}$, otherwise referred to as the "turnover number." That parameter describes the rate of release of the cleaved substrate, and is measured in terms of number of substrate molecules cleaved and released per minute. If this turnover number is low, the reaction as a whole will be slowed. The literature to date for synthetic ribozymes generally reports $k_{cat}$ values in the range of 0.5–2.1 per minute. Symons, *Ann. Rev. Biochem.*, p. 649, although one group investigating highly modified hammerhead structures, in which the flanking side-arms of the hammerhead are entirely modified to contain DNA rather than RNA, have reported slightly higher turnover rates. Hendry et al., *Nucleic Acids Res.* 20:5737–41 (1992) ($k_{cat}$ of 8.9 per minute). These catalytic rates are well below those of many enzymatic proteins, which are more typically in the range of 10–10,000 per minute. Zubay, *Biochemistry*, at 141. Although one review states that such low turnover rates "rival that of the typical DNA restriction enzymes," Long and Uhlenbeck, *FASEB J.* at 26, increased turnover rates would be greatly desired by those who would use ribozymes for either in vitro or in vivo uses.

The catalytic rate of ribozymes is further slowed when synthetic ribozymes are designed to incorporate larger regions of ribozyme/substrate base pairing necessary to provide rapid and stable binding in vivo. E.g., Taylor et al., *Nucleic Acids Res.* 20:4559 (1992); Heidenreich and Eckstein, *J. Biol. Chem.* 267:1904–1909 (1992); Bennett and Cullimore, *Nucleic Acids Res.* 20:831–837 (1992); Goodchild and Kohli, *Arch. Biochem. Biophys.* 284:386–91 (1991). Although such increased base pairing improves the specificity of the ribozyme catalytic reaction, once the substrate is cleaved the larger regions of base pairing inhibit the release of the cleavage fragments. Id. Thus, to date practical in vivo use of ribozymes has been inhibited by a perceived need to trade off specificity and stability, on the one hand, with rapid catalytic reactions, on the other.

Researchers have attempted to increase the in vivo efficacy of ribozymes by chemically modifying their structures to increase resistance to the natural degradative processes within the cell. A review of such modifications is provided by Heidenreich et al., *FASEB J.* 7:90–96 (1993). Despite some progress in the chemical modification of synthetic ribozymes, their practical usefulness remains limited, in part because of the low turnover number ($k_{cat}$) characteristic of the ribozymes known to date. This is particularly true for synthetic ribozymes which have been designed with extensive regions of substrate interaction designed to optimize the specificity of the interaction between synthetic ribozyme and substrate.

Accordingly, there exists a need for synthetic ribozymes having improved stability and rates of catalytic turnover, both for in vitro and in vivo applications.

SUMMARY OF THE INVENTION

This invention provides a synthetic catalytic ribozyme with enhanced stability and rates of product release. In general, the invention features a synthetic ribozyme polynucleotide comprising a catalytic region having endonuclease activity specific for a target polynucleotide sequence of a substrate that is linked directly or indirectly to at least one substrate binding region having a competitive binding nucleotide sequence and at least one displaceable antisense arm comprising first and second stabilization regions and a displacement region capable of forming a hybrid with the competitive binding nucleotide sequence. In one preferred embodiment of the invention, the displaceable antisense arm is a unitary, covalently linked structure. In another preferred embodiment, the displaceable antisense arm comprises a first fragment containing a first stabilization region and a second fragment containing a second stabilization region, wherein the first fragment is linked, directly or indirectly, to the first substrate binding region and the second fragment is associated only by noncovalent bonds between the first and second stabilization regions. In yet another preferred embodiment, this invention features ribozymes in which the sugar-phosphate backbone has been chemically modified.

Another aspect of this invention features a method for selecting ribozymes with enhanced rates of product release, the method comprising: constructing at least one set of synthetic ribozyme oligonucleotides comprising variable length substrate binding regions and displaceable antisense arm regions, and further comprising an inactivated catalytic site; constructing a desired substrate; contacting the set of synthetic oligonucleotides with the substrate at a temperature that is less than a preselected temperature; capturing substrate/oligonucleotide complexes and subjecting them to the preselected temperature; capturing and amplifying any oligonucleotides released at the preselected temperature; repeating these steps until a constant binding and release is found; cloning, isolating, and sequencing any oligonucleotides released after that constant binding and release is achieved; and activating the catalytic sites of any of such oligonucleotides.

In yet another aspect, this invention features a method for improving the rate of endonuclease activity of a known ribozyme having a catalytic region linked, directly or indirectly, to at least one substrate binding region, comprising: providing the ribozyme polynucleotide; obtaining a substantial portion of the nucleotide sequence of at least one substrate binding region of the ribozyme; selecting within at least one of any of the substrate binding regions a competitive binding nucleotide sequence capable of forming a first hybrid with the substrate; and modifying the ribozyme to provide at least one displaceable antisense arm linked, directly or indirectly, to the selected substrate binding region containing the competitive binding nucleotide sequence, wherein the displaceable antisense arm further comprises a first stabilization region, a second stabilization region, and a displacement region capable of forming a second hybrid with the competitive binding nucleotide sequence.

In still another aspect, this invention features a method for cleaving a target nucleotide sequence, the method comprising: providing a desired substrate; providing a synthetic ribozyme polynucleotide comprising a catalytic region having endonuclease activity specific for the target polynucleotide sequence of the substrate, at least one substrate binding region linked, directly or indirectly, to a catalytic region, with the substrate binding region further comprising a competitive binding nucleotide sequence capable of forming a first hybrid with the substrate, and at least one displaceable antisense arm linked, directly or indirectly, to the substrate binding region, with the displaceable antisense arm further comprising a first stabilization region, a second stabilization region, and a displacement region capable of forming a second hybrid with the competitive binding nucleotide sequence, and; contacting the synthetic ribozyme polynucleotide and the substrate to allow the catalytic region to cleave the substrate at its target nucleotide sequence.

The details of the invention will become apparent to those skilled in the art after having read the following detailed description of the invention.

BRIEF DESCRIPTION OF THE DRAWINGS

FIG. 1 parts a–e is a schematic representation of a portion of a synthetic ribozyme polynucleotide, displaying the relation of the substrate binding region of the ribozyme to the stabilization regions and displacement regions of the displaceable antisense arm, and alternatively to the substrate.

DESCRIPTION OF THE PREFERRED EMBODIMENTS

Detailed Description of the Invention

Figure 1A:
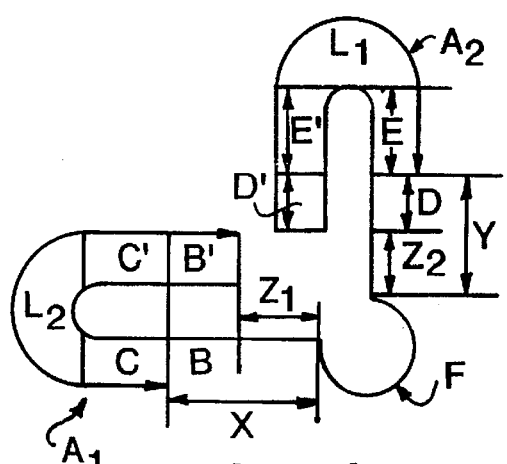
FIG. 1a depicts a ribozyme structure having two displaceable antisense arms, two substrate binding regions and a catalytic region.
Figure 1B:
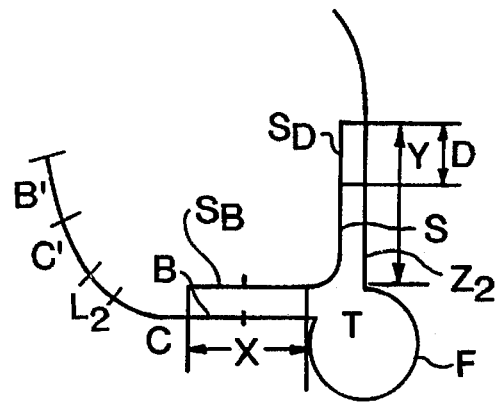
FIG. 1b depicts a substrate bound to the substrate binding region of the ribozyme.
Figure 1C:
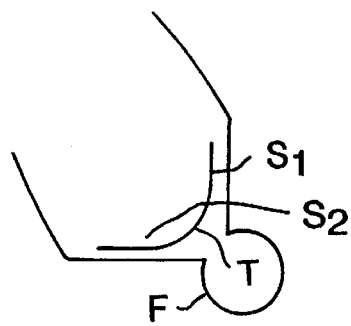
FIG. 1c depicts two bound substrate fragments after cleavage of the substrate by the ribozyme.
Figure 1D:
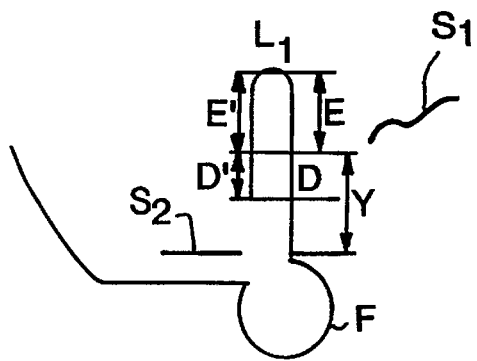
FIG. 1d depicts rehybridization of one displaceable antisense arm and corresponding displacement of one substrate fragment.
Figure 1E:
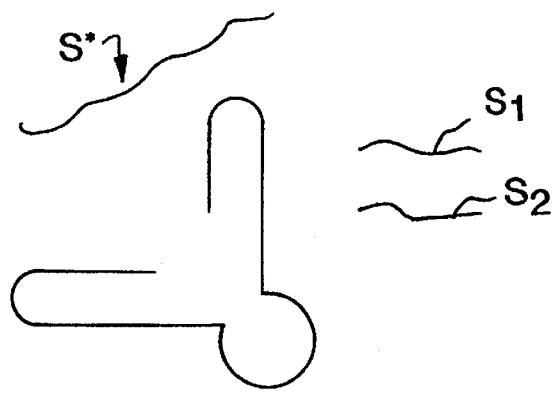
FIG. 1e depicts the rehybridization of the second displaceable antisense arm and corresponding displacement of the second substrate fragment.

As used herein, a "ribozyme polynucleotide" is a polynucleotide that has the ability to catalyze the cleavage of a polynucleotide substrate. In general, it will have a first end and a second end, wherein the first end may be either the 5' or the 3' end of the polynucleotide. It further comprises a catalytic region, at least one substrate binding region, and at least one displaceable antisense arm. It may be classified as, but is not limited to, ribozyme structures of the hammerhead, hairpin, HDV, RNAase P, L-19 IVS, Group I, or Group II types. It may be "natural," i.e., naturally occurring in nature, "synthetic," i.e., designed and synthesized in order to bind and cleave a desired substrate, or "known," i.e., either a natural or synthetic ribozyme that has been previously sequenced and characterized.

A generalized depiction of the synthetic ribozyme polynucleotide of the claimed invention is provided in FIG. 1. Although FIG. 1 depicts a ribozyme having a hammerhead structure modified to contain two displaceable antisense arms, it is not intended to suggest that the invention is limited to this particular structure. FIG. 2 provides a diagrammatic representation of a ribozyme of the hairpin variety. Again, it is not intended to suggest that the invention is limited to this particular structure.

Substrate cleavage is performed by the "catalytic region" F of the ribozyme polynucleotide. Generally, the catalytic region will contain a region of highly conserved bases that are believed to be necessary to ensure proper interaction with the substrate. Long and Uhlenbeck, FASEB J. 7:25 (1993), and Symons, Ann. Rev. Biochem., 61:641 (1992), provide thorough discussions of the sequence requirements of various catalytic regions. The disclosures of those references are incorporated herein in their entirety. For example, in ribozymes of the hammerhead type, the consensus sequence is reported to be 5'-CUGANGAN:NGAAAC, wherein N:N designates the first base pair of the hammerhead helix III. Id. at 646. A consensus sequence for the axehead structure is depicted at id. p. 664, FIG. 12. The hairpin ribozyme requires the sequence 5'-NN...NNGAA(GorC)NNNNCNNNNNGAAACAN...3'(SEQ ID NO:3), wherein Helix 1 and Helix 4 occur at the ellipses. Long and Uhlenbeck, FASEB J. at 28. Alternatively, portions of the catalytic region may be provided by the substrate rather than the ribozyme. Id. at 27 FIG. 2. The catalytic region of the HDV ribozyme is reported as 5'-CCGNNCUGGG (SEQ ID NO:4). Perrotta and Been, Biochemistry 31:16, 17 (1992); see also U.S. Pat. No. 5,225,337, FIG. 2b (sequences containing delta ribozyme activity) and U.S. Pat. No. 5,225,347, FIG. 3 (proposed secondary structure of 110 nucleotide HDV subfragment possessing autocatalytic activity). The catalytic region for an RNAase P ribozyme is described in U.S. Pat. No. 5,168,053, FIG. 2, with a reported invariant 5'-NCCA region. The minimum active site for L-19 IVS ribozyme catalytic activity is described in U.S. Pat. No. 5,168,053, Col. 16, line 46, through Col. 17, line 4, and a diagrammatic representation of the catalytic site is given in FIG. 2, reporting a conserved sequence 5'-GGAGGG, which hybridized with the required substrate sequence CUCU. See also U.S. Pat. No. 5,116,742, FIG. 8 (describing interaction of $G^{414}$ with the bound L-19 IVS ribozyme substrate).

Figure 2:
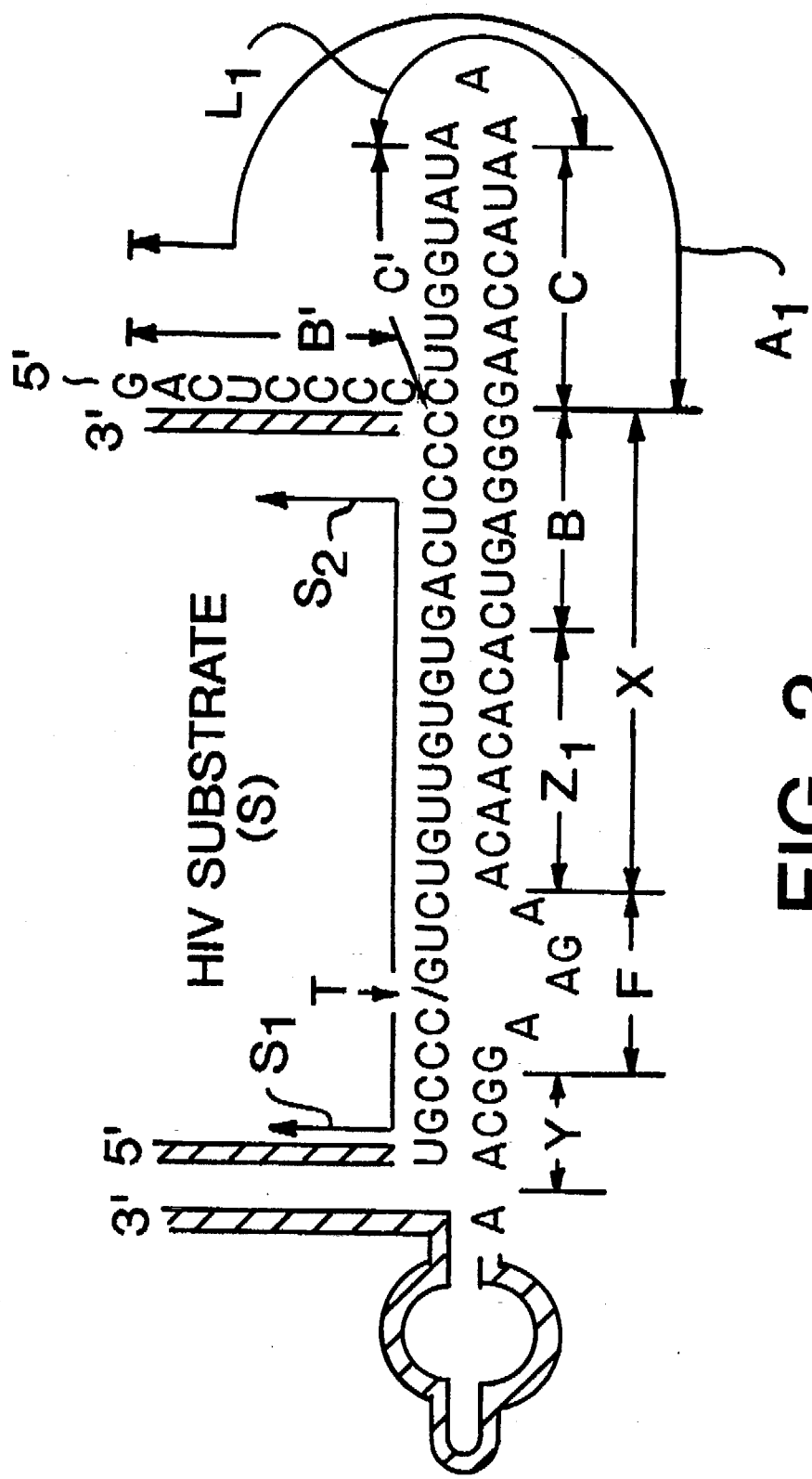
FIG. 2 is a diagrammatic representation of a ribozyme of the hairpin variety, modified to contain one displaceable antisense arm.

Referring to FIG. 1a, an example of the structure of the ribozyme polynucleotide of this invention is now described in further detail. This diagrammatic representation is based on the highly conserved hammerhead structure described by Haseloff, U.S. Pat. No. 5,254,678, which is incorporated by reference in its entirety. However, the ribozyme structure has been modified to contain two "displaceable antisense arms," designated generally as $A_1$ and $A_2$. The displaceable antisense arms compete with the substrate for binding to the substrate binding regions, as will be described in further detail herein.

Regardless of the ribozyme's general structural classification, the ribozyme polynucleotide will have at least one "substrate binding region," designated in FIG. 1 as X, which has a competitive binding nucleotide sequence B that hybridizes with a complementary region $S_B$ of substrate S. (In FIG. 1a, the ribozyme contains a second, structurally similar displacement arm $A_2$ and a second, analogous substrate binding region designated as Y that hybridizes with the complementary region $S_D$ of substrate S.) Substrate binding region X is linked to the catalytic region F. Generally, it will be directly linked, for example by covalent bonds. Alternatively, it may indirectly linked, for example, by an intervening polynucleotide region, that does not inhibit the necessary spatial relation of substrate S and catalytic region F. The length of the substrate binding region X may vary, with the minimum length determined by the degree of specificity required and the maximum length determined by factors including the temperature of the reaction and the nucleotide composition of the substrate binding region. Generally, when one displacement arm is used, the substrate binding region may be 4–40 nucleotides in length, or more preferably, 8–20 nucleotides in length. A second substrate binding region with no associated displacement arm would generally be 1–12 nucleotides in length, or more preferably 5–8 nucleotides in length. If two displacement arms are used, each of the substrate binding region may be 4–40 nucleotides in length, or more preferably, 4–16 nucleotides in length.

The substrate binding region of this invention contains a "competitive binding nucleotide sequence" B that can hybridize with either the region $S_B$ of substrate S or with the "displacement region" B' of the displaceable antisense arm $A_1$. The displacement region B' is a nucleotide sequence that is complementary with the competitive binding nucleotide sequence B of the substrate binding region X (and thus is substantially similar to regions$_B$ of substrates). The length of the substrate binding region and the displacement region may vary. Generally, when one displacement arm is used, the displacement region and the competitive binding nucleotide sequence may be 2–20 nucleotides in length, or more preferably, 4–10 nucleotides in length. If two displacement arms are used, each of the substrate binding region generally may be 2–20 nucleotides in length, or more preferably, 4–10 nucleotides in length.

The displaceable antisense arm $A_1$ comprises the displacement region B', a first "stabilization region" C, a second stabilization region C', and optionally may contain a nonhybridizing region $L_1$. The first stabilization region is linked, either directly or indirectly, to the substrate binding region. The first stabilization region C is substantially complementary to a second stabilization region C' of the displaceable antisense arm, and the two regions will hybridize in the absence of bound substrate. As can be seen in FIG. 1a, a nucleotide or sequence of nucleotides $L_1$ may intervene between the first and second stabilization regions. $L_1$ also may use some other covalent linking means, for example an ethylene glycol linker. Alternatively, if the first and second stabilization regions provide a hybridization region of sufficient length so as to not completely dissociate from one another upon substrate binding, $L_1$ is not required. The length of the first and second stabilization regions may vary, but generally will be within the range of 1–100 nucleotides, or, more preferably, 2–20 nucleotides.

The polynucleotide substrate S will contain a "target polynucleotide sequence" T, which is defined as a sequence that is cleaved by the catalytic region of a ribozyme. Substrate S has regions $S_B$ and $S_D$ that hybridize with the corresponding competitive binding nucleotide sequences B and D within substrate binding regions X and Y, respectively. Accordingly, $S_B$ and $S_D$ are substantially similar to displacement regions B' and D' of displaceable antisense arms $A_1$ and $A_2$.

In many instances, substrate S will be a known polynucleotide sequence. For example, Ojwang et al. reported use of a hairpin ribozyme cleaving the N*GUC sequence (in which GUC is described as a required sequence and cleavage occurs at *) to target and cleave the 5' leader sequence of HIV-1 at the position +111/112 relative to the transcription initiation site. *Proc. Natl. Acad. Sci. USA* 89:10802–10806 (1992). Rossi et al., U.S. Pat. No. 5,144,019, the disclosure of which is incorporated herein in its entirety, describes the use of hammerhead ribozymes recognizing the sequence GAAAC(X)$_n$GU, in which X is any nucleotide and n may have any value. See Col. 2, lines 39–50.

Once a target polynucleotide sequence is chosen, a ribozyme containing at least one displaceable antisense arm can easily be designed using known ribozyme consensus sequence information and base pairing rules. For example, a target substrate such as Hepatitis C virus may contain the target polynucleotide sequence 5'NNGUC*NNN3', wherein GUC is the consensus sequence for a ribozyme of the hammerhead type, and * indicates the cleavage site. Symons, *Ann. Rev. Biochem.* at 646. A synthetic ribozyme of the hammerhead type is then designed. First, it provides the consensus catalytic region 5'. . .CUGANGA. . .GAAAC. . .3'(SEQ ID NO:5), wherein the non-conserved helical regions are designated by ellipses. Id. Using conventional base pairing rules, the ribozyme is then designed to provide nucleotides flanking the 5' and 3' sides of the catalytic region that are complementary to the nucleotides flanking the conserved GUC* target sequence of the substrate. These two flanking regions of the ribozyme are the "substrate binding regions." Thus, the substrate binding regions are designed to align the 3'AC terminal portion of the hammerhead consensus catalytic region to align with the complementary, conserved GU region of the substrate, thus spatially orienting the substrate for cleavage. Id. Finally, the ribozyme is designed to provide at least one displaceable antisense arm. To do so, one first designates a portion of the substrate binding region distal from the catalytic region (i.e., either the 5' or the 3' end of the substrate binding region) as the "competitive binding nucleotide sequence," and designs a "displacement region" that is substantially similar to the substrate region and thus would hybridize with the ribozyme in that region. The remainder of the displaceable antisense arm then simply is designed to contain two regions that hybridize with one another (the first and second "stabilization regions"), with an optional linking region between the two stabilization regions if those regions would otherwise dissociate upon ribozyme binder of substrate. The first stabilization region is linked to the substrate binding region. The end result is a molecule that is designed to base pair with itself in the absence of substrate, but to dissociate and allow the substrate to bind to the ribozyme. When the ribozyme cleaves the substrate, the two resultant substrate fragments then dissociate, or are "ejected," by the rehybridization of the first and second stabilization regions and of the substrate binding region and the displacement region.

Variations on this basic description are suggested by the literature. For example, in some instances the substrate itself may provide a portion of the consensus catalytic region. Jeffries and Symons, *Nucleic Acids Res.* 17:1371, 1373 (1989). Alternatively, the ribozyme may be constructed of two or more separate oligonucleotides that base pair in the correct orientation to provide the requisite catalytic region consensus sequence. Id.

The kinetic process of ribozyme binding, cleavage, and displacement of substrate molecules is depicted in FIG. 1. In FIG. 1a, the representative synthetic ribozyme polynucleotide is shown in the absence of substrate. FIG. 1b depicts the substrate S bound to substrate binding regions X and Y and the dissociation of the displacement regions B' and D' from competitive binding nucleotide sequences B and D. FIG. 1c depicts the substrate S cleaved at target nucleotide sequence T, yielding two "cleavage fragments" $S_1$ and $S_2$. FIG. 1d depicts rehybridization of the first and second stabilization regions E and E', the hybridization of displacement region D' of displaceable antisense arm $A_2$ to the competitive binding nucleotide sequence D of substrate binding region Y and the corresponding displacement of cleavage fragment $S_1$. FIG. 1e depicts the analogous dissociation of cleavage fragment $S_2$, thereby preparing the synthetic ribozyme polynucleotide to bind to and cleave the next substrate molecule S*.

FIG. 2 represents a hairpin ribozyme (SEQ ID NO:6) designed to cleave the 5' untranslated leader sequence of HIV (SEQ ID NO:7). The ribozyme has been modified to contain one displaceable antisense arm $A_1$. The substrate binding region X again contains the competitive binding nucleotide sequence B, and is linked to an exemplary first stabilization region C. The exemplary second stabilization region C', which hybridizes with the first stabilization region C, is linked to C with a short intervening nucleotide sequence $L_1$. Displacement region B', which is substantially identical to the $S_B$ region of the HIV substrate S, may hybridize with the competitive binding nucleotide sequence B. The ribozyme also contains a second substrate binding region Y.

Referring generally to FIG. 1, the displaceable antisense arm is designed to enhance the rate of cleavage fragment release because the stability of the hybrid formed by the first and second stabilization regions (C/C') and by the competitive binding nucleotide sequence and displacement region (B/B') is less than that of the hybrid formed by the substrate binding region X and the substrate S, but greater than that of the substrate binding region X and the cleavage fragment of the substrate, $S_2$.

In general, the synthetic polynucleotide ribozyme may have one or more substrate binding regions, and one or more displaceable antisense arms. A synthetic ribozyme polynucleotide containing more than one substrate binding region need not have a corresponding displaceable antisense arm for each region. However, each substrate binding region may only have a single corresponding displaceable antisense arm.

THE DESIGN OF SYNTHETIC RIBOZYMES WITH ENHANCED RATES OF CLEAVAGE FRAGMENT RELEASE

As those in the art appreciate, the general approach diagrammed in FIG. 1 readily adapts itself to many structural variations. For example, the synthetic ribozyme polynucleotide of this invention may be one contiguous polynucleotide sequence, in which case the ribozyme is referred to as a "unitary" molecule. Alternatively, the ribozyme may be made of two or more polynucleotide sequences that hybridize to form the functional ribozyme. In such a case, the synthetic ribozyme is said to be comprised of ribozyme "fragments." Preparation and use of such ribozyme fragments in a hammerhead structure are described by Koizumi et al., *Nucleic Acids Res.* 17:7059-7071 (1989). Preparation and use of ribozyme fragments in a hairpin structure are described by Chowrira and Burke, *Nucleic Acids Res.* 20:2835 (1992). Both unitary molecules and ribozyme fragments are within the scope of this invention. Another structural variation on the general approach is to provide more than one displaceable antisense arm, as depicted in FIG. 1, in order to further facilitate the release of the substrate cleavage fragments from each of the corresponding substrate binding regions.

The invention described herein is applicable to a wide variety of ribozyme structures, as will be evident to those skilled in the art. For example, a hammerhead ribozyme is depicted diagrammatically in FIG. 1. A hairpin ribozyme structure with an added displaceable antisense arm is depicted diagrammatically in FIG. 2. The invention may also be applied to other ribozyme structures, including without limitation the Hepatitis Delta Virus ribozyme described by Robertson et al., U.S. Pat. No. 5,225,337 (which reference is incorporated herein in its entirety), the Tetrahymena L-19 IVS RNA described by Cech et al., U.S. Pat. No. 5,116,742 (which reference is incorporated herein in its entirety), and the RNAase P ribozyme described in Altman, U.S. Pat. No. 5,168,053 (which reference is incorporated herein in its entirety). Particularly, the selected ribozyme structure will have at least one substrate binding region, wherein the substrate binding region can be modified to add a displaceable antisense arm. The substrate binding region may be modified by linking the displacement arm in linear arrangement, or alternatively, may be prepared as a branched structure. E.g., Horn and Urdea, *Nucleic Acids Res.* 17:6959-67 (1989).

The basic structure of the ribozymes may also be chemically altered in ways quite familiar to those skilled in the art. For example, the 2' hydroxyl of the ribose moiety may be chemically altered. Heidenreich et al., *FASEB J.* at 92. In particular, this location may be selectively modified with O-methyl or O-allyl groups. Shibahara et al., *Nucleic Acids Res.* 17:239 (1989), Paollella et al., *EMBO J.* 11:1913 (1992). Pieken et al., *Science* 253:314 (1991), modified the 2' position with 2'-amino and 2'-fluoro groups. Many researchers also have investigated the effect of substituting 2'-deoxynucleotides at a variety of positions. E.g., Williams et al., *Proc. Nat'l Acad. Sci. USA* 89:918 (1992); Fu et al., *Proc. Nat'l Acad. Sci. USA* 89:3985 (1992); Olsen et al., *Biochemistry*, 30:9735 (1991); Yang et al., *Biochemistry* 31:5005 (1992); Perreault et al., *Nature* 344:565 (1990). Alternatively, arabinose-based nucleotides may be substituted for ribose-based nucleotides.

Although not all ribose moieties may be modified at the 2' position without adverse effect on catalytic ability, the literature provides extensive guidance to those skilled in the art as to which positions should remain unchanged. For example, using the standard hammerhead numbering system, *Nucleic Acids Res.* 20:3252 (1992), deoxynucleotide substitution at the $G^9$, $A^{13}$, and $U^7$ significantly decreased catalytic activity in ribozymes of the hammerhead structure. Perreault et al., *Biochemistry* 30:4020 (1991). Fu et al., supra, reported a drastic decrease of cleavage efficiency for hammerhead ribozymes substituted at the $G^{10}$ or $G^{13}$ position. Williams, supra, reported that substitution of the non-conserved nucleotides within a hammerhead ribozyme caused little alteration in catalytic ability. Two groups have described a hammerhead ribozyme in which the hybridizing regions are entirely composed of 2'-deoxynucleotides, and which display a significant increase in the catalytic rate. Hendry et al., *Nucleic Acids Res.* 20:5737 (1992); Taylor et al., *Nucleic Acids Res.* 20:4559 (1992).

Alternatively, the internucleotidic phosphate groups of the ribozyme may be selectively replaced with phosphorothionate. Heidenreich, supra, at 90-92. Substitution with thiophosphates 5' to all guanosines, cytidines, and uridines were reported to have little effect on the catalytic rate of the ribozyme, while substitution of multiple adenosines significantly decreased the catalytic rate. Chowrira and Burke, *Nucleic Acids Res.* 20:2835 (1992). Slim and Gait, *Nucleic Acids Res.* 19:1183 (1991), described a method of chemically synthesizing oligoribonucleotides containing a single phosphorothionate linkage in a defined stereochemical position. Ruffner and Uhlenbeck, *Nucleic Acids Res.* 18:6025 (1990), identified four phosphates in the conserved core of a hammerhead ribozyme which cannot be modified without large reductions in cleavage rates.

METHODS OF MAKING SYNTHETIC RIBOZYMES WITH ENHANCED RATES OF CLEAVAGE FRAGMENT RELEASE

Synthetic ribozymes may be synthesized directly as RNA using commercially available compounds on an automated synthesizer. In the event that a sequence is too long for efficient direct synthesis, two fragments may be joined by RNA ligase methods. Alternatively, the DNA encoding for the desired ribozyme may be designed and constructed by standard recombinant DNA techniques well known to those skilled in the art. E.g., Maniatis et al. (1989), *Molecular Cloning: A Laboratory Manual* (Cold Spring Harbor Labs, Cold Spring Harbor, N.Y.).

The design and construction of an HIV-specific ribozyme of the hairpin type is used by way of example. The ribozyme is based upon the minimum catalytic center of the negative strand of the tobacco ringspot virus. Hampel and Tritz, *Biochemistry* 28, 4929-4933 (1989). See Ojwang et al.,

*Proc. Natl. Acad. Sci. USA* 89:10802–10806 (1992), the disclosure of which is incorporated by reference in its entirety. Based on the clone HXB2, Ratner et al., *Nature* 313:277–284 (1985), a N*GUC target sequence is located on the 5' leader sequence of HIV-1 at the position +111/112 relative to the transcription initiation site, within the sequence UGCCCGUCUGUUGUGU (SEQ ID NO:8) of the clone HXB2. FIG. 2 shows the incorporation of this sequence into a hairpin ribozyme that has been modified to contain a model displacement arm.

The ribozyme of FIG. 2 may be constructed as follows. Double-stranded oligodeoxyribonucleotides containing the desired ribozyme sequences are chemically synthesized, with each end being flanked by a suitable restriction endonuclease site. The oligonucleotides are then cloned into a corresponding suitable plasmid. Correct clones are identified by filter hybridization and confirmed by DNA sequencing. DNA fragments are cloned into a plasmid containing a suitable promotor, for example the human β-actin promoter or the adenovirus VA1 gene promotor. Yu et al., *Proc. Natl. Acad. Sci. USA* 89:6340–6344 (1993). The gene containing the DNA encoding for the ribozyme is then expressed.

In order to increase stability or alter properties of the model HIV ribozyme, ribonucleotides in catalytically noncritical positions can be replaced by deoxyribonucleotides, modified ribonucleotides (e.g., 2'-O-methyl), or nonnucleotidic components. Methods for making such chemical modifications are familiar to those skilled in the art, as exemplified by the references collected and summarized in Heidenreich et al., *FASEB J.* 7:90–96 (1993).

Alternatively, a protocol which provides for in vivo production of the ribozyme may be employed. For example, DNA encoding the desired ribozyme may be chemically synthesized and cloned into suitable plasmids. A suitable promotor, e.g. the human tRNA$^{Val}$ promoter and adenovirus VA1 promoter, may then be cloned into the plasmid upstream of the ribozyme. The plasmid may then be digested, inserted into a suitable retroviral vector, and transfected into the target cell. Yu et al. (1993), supra.

A similar strategy may be employed by selecting a suitable cleavage site in the 5' untranslated region of the Hepatitis C virus. See Cha et al., *Proc. Nat'l. Acad. Sci. USA* 89:7144 (1992) and Cha et al., *J. Clin. Microbiol.* 29:2528 (1991). A known ribozyme, e.g., the nuclease resistant chimeric ribozyme of Shimayama and Nishikawa, *Nucleic Acids Res.* 21:2605 (1993), may be modified to contain a displaceable antisense arm that facilitates release of the Hepatitis C virus cleavage products.

METHOD OF SELECTING SYNTHETIC RIBOZYME WITH OPTIMIZED RATES OF CLEAVAGE FRAGMENT RELEASE

Synthetic ribozymes having optimized rates of cleavage and turnover may be selected using repeated cycles of in vitro selection and amplification. In vitro selection and amplification of large pools of sequences with the desired properties has been shown to be useful for the isolation of such molecules. Bartel and Szostak, *Science* 261:1411–1418 (1993). In a modification of that method, a large pool of compounds with potentially beneficial ribozyme activity will initially be made as described above, but with inactive catalytic sites.

Figure 3:
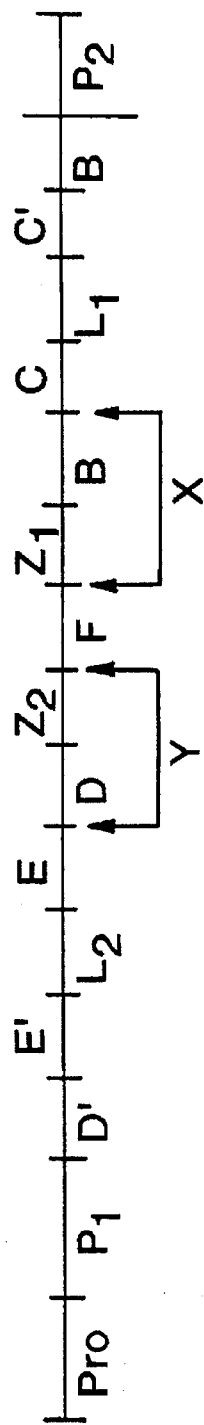
FIG. 3 is a diagrammatic representation of a synthetic oligonucleotide used for isolating optimized synthetic ribozymes.

Referring to FIG. 3, two sets of synthetic oligonucleotides with variable lengths for each of the two displacement arm regions $Z_1$, B, C, $L_1$, C', B' and $Z_2$, D, E, $L_2$, E', D', along with catalytic region F, are constructed. (The letter designations B–F correspond to the representative ribozyme of FIG. 1.) "Pro" represents a promoter, preferably $T_7$. $P_1$ and $P_2$ represent PCR primer sites, generally comprising 15–20 bases each. Using probable ranges disclosed herein, variable length oligonucleotides can be produced by one of two ways: a) by removing a portion of the solid phase after each step of the variable portion of the synthesis, then recombining; or b) by using levulinic anhydride for capping, then removing with hydrazine:acetic acid:pyridine:H$_2$O. After the variable position is completed, the synthesis is continued. See e.g., Horn and Urdea, *Tetrahedron Letters* 27:2933–2937 (1986), and *Nucleic Acids Res. Symposium Series*, 16:153 (1985). Then, a total ribozyme transcription element is constructed, whereby Pol 1 and nucleotide triphosphates are filled in, ligated, and transcribed. The substrate RNA complementary to D/Z$_2$/Z$_1$/B is then constructed either synthetically or enzymatically. Biotinylated nucleotides are incorporated. The transcribed ribozyme pool and the substrate are then combined at a lower temperature than desired for product release, e.g., 10°–15 C.° below physiological temperature. The complexes are captured on streptavidin beads, washed, and then subjected to the desired temperature, e.g., physiological temperature. Using ProP$_1$ and P$_2$' PCR primers, the released material is amplified. The process of transcription, binding, and release is repeated until a constant binding and release is found. The released product is then cloned using P$_1$ and P$_2$' PCR primers adapted with restriction sites for cloning into a T$_7$ promoter-containing vector. The clones are isolated and sequenced. Using in vitro mutagenesis techniques well known to those skilled in the art, the inactive catalytic sites are converted to active catalytic sites. Finally, the specific ribozymes are tested for K$_{cat}$ and functionality.

Figure 4:
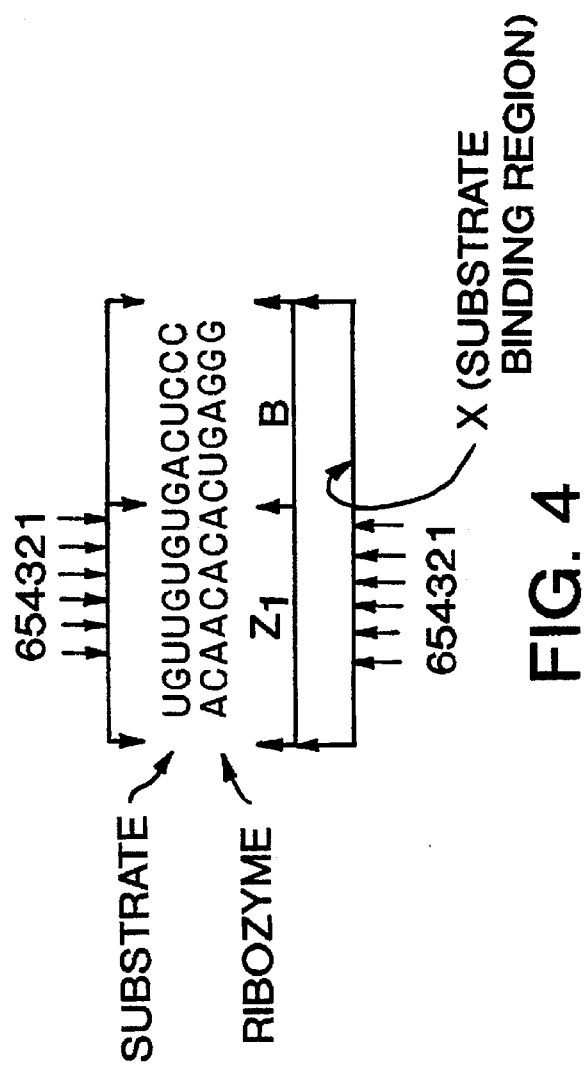
FIG. 4 is a diagrammatic representation of a method for optimizing a ribozyme (SEQ ID NO:1) specific for HIV (SEQ ID NO:2).

This protocol may be used to produce the HIV-specific ribozyme, discussed above. As a first attempt, the length and composition of C, C', F would be maintained while the length of $Z_1$, B, and B' would be altered. For instance, the designs shown in FIG. 4 can be constructed, wherein FIG. 4 corresponds to region A$_1$ of FIG. 2. The numerals 1,2,3, 4,5,6 indicate the change in junction between $Z_1$ and the substrate. So, in design 1 the tail of the ribozyme, B', has the sequence GACUCCC (7 bases); in design 2, B' is UGACUCCC (8 bases) and Z$_1$ is shorter by one base, A. The efficiencies of each design can be assessed (i.e., K$_{cat}$ and K$_M$ studies). E.g., Hampel et al., *Nucleic Acids Res.* 18:299–304 (1990). Procedures for construction, characterization, and in vitro transcription of the ribozyme are given in Ojwang et al. (1992), and are discussed above.

METHODS OF USING SYNTHETIC RIBOZYMES WITH ENHANCED RATES OF CLEAVAGE FRAGMENT RELEASE a) In vitro uses:

In vitro uses of ribozymes have been well described by Altman et al., U.S. Pat. No. 5,168,053, Cech et al., U.S. Pat. No. 5,116,742, Robertson et al., U.S. Pat. No. 5,225,337, and Haseloff, U.S. Pat. No. 5,254,678, all of which are incorporated by reference. The ribozymes described herein are interchangeable in those protocols, but will provide enhanced catalytic rates. In addition, for in vitro protocols involving ribozymes which are unstable or difficult to synthesize, it will be advantageous to complete the protocol with a more efficient ribozyme.

b) In vivo uses:

Ribozymes show great therapeutic promise for altering viral replication in vivo. Such uses have been discussed in, e.g., Altman et al., U.S. Pat. No. 5,168,053, Robertson et al., U.S. Pat. No. 5,225,337, and Haseloff, U.S. Pat. No. 5,254,678, all of which are incorporated by reference. The therapeutic ribozyme is exposed to the target polynucleotide in one of two general ways. First, the ribozyme may be isolated in the laboratory and packaged in a suitable delivery vehicle, for example liposomes. Taylor et al., *Nucleic Acids Res.* 20:4559 (1992). Such exogenous therapeutic approaches generally require that the ribozyme be modified to stabilize against degradation. Second, the DNA encoding the ribozyme of interest is incorporated into a vector with a suitable promotor, and delivered to the target cell. Such an endogenous delivery technique is described in Ojwang et al. (1992) and Yu et al. (1993), for example. Variations in both the endogenous and exogenous delivery techniques are familiar to those skilled in the art.

The biological activity of the ribozyme can be assessed in several ways. In vivo studies for anti-HIV activity can be conducted using transcribed or isolated HIV RNA. Transient transfection systems have been described. Ojwang et al. (1992). HIV-infected cells can be employed to study intracellular localization and efficiency of ribozymes. Appropriate animal models such as the SCID mouse, the green tail macaque, or the chimpanzee can be explored.

The stability and distribution of the ribozyme could be modified by use of targeting agents such as liposomes, conjugates targeting hepatocytes such as described by Wu et al., *J. Biol. Chem.* 267:12436 (1992), or cholesterol modifications. E.g., Grayaznov et al., *Nucleic Acids Res.* 21:5909 (1993).

In light of the above description, it is anticipated that alterations and modifications thereof will be apparent to those skilled in the art. Such other embodiments are within the following claims.

---

What is claimed is:

1. A synthetic ribozyme polynucleotide having a first end and a second end, comprising from said first end to said second end:
   a catalytic region having endonuclease activity specific for a target polynucleotide sequence of a substrate;
   a first substrate binding region linked to said catalytic region, said first substrate binding region comprising a first competitive binding nucleotide sequence capable of forming a first hybrid with said substrate; and
   a first displaceable antisense arm linked to said first substrate binding region, wherein said first displaceable antisense arm comprises a first stabilization region and a second stabilization region, said first stabilization region being capable of hybridizing with said second stabilization region, and a first displacement region capable of forming a second hybrid with said competitive binding nucleotide sequence.

2. The synthetic ribozyme polynucleotide of claim 1 wherein said synthetic ribozyme is a unitary molecule.

3. The synthetic ribozyme polynucleotide of claim 1 wherein said first displaceable antisense arm comprises a first fragment containing said first stabilization region and a second fragment containing said second stabilization region, wherein said first fragment is linked to said first substrate binding region, and wherein said second fragment is associated only by noncovalent bonds between said first and said second stabilization regions.

4. The synthetic ribozyme polynucleotide of claim 1 wherein said first stabilization region and said first competitive binding nucleotide sequence are separated by at least one nucleotide.

5. The synthetic ribozyme polynucleotide of claim 1, further comprising a second substrate binding region linked to said catalytic region at said first end.

6. The synthetic ribozyme polynucleotide of claim 5, further comprising a second displaceable antisense arm linked to said second substrate binding region.

7. The synthetic ribozyme polynucleotide of claim 1 wherein said first substrate binding region is directly linked by covalent bonds to said catalytic region.

8. The synthetic ribozyme polynucleotide of claim 1 wherein said first displaceable antisense arm is directly linked by covalent bonds to said first substrate binding region.

9. The synthetic ribozyme polynucleotide of claim 1 wherein said first substrate binding region is indirectly linked by an intervening polynucleotide region to said catalytic region.

10. The synthetic ribozyme polynucleotide of claim 1 wherein said first displaceable antisense arm is indirectly linked by an intervening polynucleotide region to said first substrate binding region.

11. The synthetic ribozyme polynucleotide of claim 1 wherein said synthetic ribozyme polynucleotide is of the hammerhead structure.

12. The synthetic ribozyme polynucleotide of claim 1 wherein said synthetic ribozyme polynucleotide is of the hairpin structure.

13. A composition which comprises the synthetic ribozyme polynucleotide of claim 1 in a carrier.

14. A synthetic ribozyme polynucleotide comprising at least one displaceable antisense arm, wherein the sugar-phosphate backbone of said synthetic ribozyme polynucleotide has been chemically altered.

15. The synthetic ribozyme polynucleotide of claim 14 wherein at least one ribonucleotide is replaced with a deoxynucleotide.

16. The synthetic ribozyme polynucleotide of claim 14 wherein at least one ribonucleotide is modified at the 2'-position.

17. The synthetic ribozyme polynucleotide of claim 16 wherein said at least one ribonucleotide is selected from a group consisting of 2'-fluoro, 2'-amino, 2'-O-alkyl, and 2'-O-allyl.

18. The synthetic ribozyme polynucleotide of claim 17 wherein said at least one ribonucleotide is 2'-O-methyl.

19. The synthetic ribozyme polynucleotide of claim 14 wherein selected ribonucleotides of said sugar-phosphate backbone are phosphorothionated.

20. A method for producing synthetic ribozyme polynucleotides, comprising the steps of:
   constructing at least one set of synthetic ribozyme oligonucleotides comprising variable length substrate binding regions and displaceable antisense arm regions, and further comprising an inactivated catalytic site;
   constructing a desired substrate;
   contacting said set of synthetic oligonucleotides with said substrate at a temperature which is less than a preselected temperature;
   capturing complexes of said substrate and said oligonucleotides;
   subjecting said complexes to said preselected temperature;
   capturing and amplifying any oligonucleotides released at said preselected temperature;
   repeating the steps of constructing synthetic ribozyme oligonucleotides, contacting with substrate, capturing complexes, subjecting complexes to said preselected temperature, and capturing and amplifying released complexes, until a constant binding and release is found;
   cloning, isolating, and sequencing any oligonucleotides released after said constant binding and release is achieved; and
   activating the catalytic sites of any oligonucleotides released after said constant binding and release is achieved.

21. A method of cleaving a target nucleotide sequence of a substrate, comprising the steps of:
   providing said substrate;
   providing a synthetic ribozyme polynucleotide having a first end and a second end, comprising from said first end to said second end a catalytic region having endonuclease activity specific for said target polynucleotide sequence and a first substrate binding region linked to said catalytic region, said substrate binding region further comprising a first competitive binding nucleotide sequence capable of forming a first hybrid with said substrate, and a first displaceable antisense arm linked to said substrate binding region, said first displaceable antisense arm further comprising a first stabilization region, a second stabilization region, and a first displacement region capable of forming a second hybrid with said first competitive binding nucleotide sequence; and
   contacting said synthetic ribozyme polynucleotide and said substrate to allow said catalytic region to cleave said substrate at said target nucleotide sequence.

22. The method of claim 21 wherein said synthetic ribozyme polynucleotide is a unitary molecule.

23. The method of claim 21 wherein said first displaceable antisense arm comprises a first fragment containing said first stabilization region and a second fragment containing said second stabilization region, wherein said first fragment is linked to said first substrate binding region, and wherein said second fragment is associated only by noncovalent bonds between said first and said second stabilization regions.

24. The method of claim 21 wherein said first stabilization region and said first competitive binding nucleotide sequence are separated by at least one nucleotide.

25. The method of claim 21, further comprising a second substrate binding region linked to said catalytic region at said first end.

26. The method of claim 25, further comprising a second displaceable antisense arm linked to said second substrate binding region.

27. The method of claim 21 wherein said synthetic ribozyme polynucleotide is of the hammerhead structure.

28. The method of claim 21 wherein said synthetic ribozyme polynucleotide is of the hairpin structure.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:1:

GGGAGUCACA CAACA 15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:2:

UGUUGUGUGA CUCCC 15

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:3:

NNNNGAASNN NNCNNNNGAA ACAN 24

( 2 ) INFORMATION FOR SEQ ID NO:4:

( i ) SEQUENCE CHARACTERISTICS:
        ( A ) LENGTH: 10 base pairs
        ( B ) TYPE: nucleic acid (C) STRANDEDNESS: single
(D) TOPOLOGY: linear (i i) MOLECULE TYPE: RNA (genomic)

(x i) SEQUENCE DESCRIPTION: SEQ ID NO:4:

CCGNNCUGGG 10

(2) INFORMATION FOR SEQ ID NO:5:

(i) SEQUENCE CHARACTERISTICS:
(A) LENGTH: 12 base pairs
(B) TYPE: nucleic acid
(C) STRANDEDNESS: single
(D) TOPOLOGY: linear (i i) MOLECULE TYPE: RNA (genomic)

(i x) FEATURE:
(A) NAME/KEY: A
(B) LOCATION: 7
(D) OTHER INFORMATION: /label=variable
/ note= an intervening sequence Nx of any length
may be inserted between nucleotides 7 and 8

(x i) SEQUENCE DESCRIPTION: SEQ ID NO:5:

CUGANGAGAA AC 12

(2) INFORMATION FOR SEQ ID NO:6:

(i) SEQUENCE CHARACTERISTICS:
(A) LENGTH: 50 base pairs
(B) TYPE: nucleic acid
(C) STRANDEDNESS: single
(D) TOPOLOGY: linear (i i) MOLECULE TYPE: RNA (genomic)

(x i) SEQUENCE DESCRIPTION: SEQ ID NO:6:

GACUCCCCUU GGUAUAAAAU ACCAAGGGGA GUCACACAAC AAGAAGGCAA 50

(2) INFORMATION FOR SEQ ID NO:7:

(i) SEQUENCE CHARACTERISTICS:
(A) LENGTH: 23 base pairs
(B) TYPE: nucleic acid
(C) STRANDEDNESS: single
(D) TOPOLOGY: linear (i i) MOLECULE TYPE: RNA (genomic)

(x i) SEQUENCE DESCRIPTION: SEQ ID NO:7:

UGCCCGUCUG UUGUGUGACU CCC 23

(2) INFORMATION FOR SEQ ID NO:8:

(i) SEQUENCE CHARACTERISTICS:
(A) LENGTH: 16 base pairs
(B) TYPE: nucleic acid
(C) STRANDEDNESS: single
(D) TOPOLOGY: linear (i i) MOLECULE TYPE: RNA (genomic)

(x i) SEQUENCE DESCRIPTION: SEQ ID NO:8:

UGCCCGUCUG UUGUGU 16